United States Patent
Tran et al.

[11] Patent Number: 6,142,947
[45] Date of Patent: Nov. 7, 2000

[54] ULTRASOUND PROBE AND RELATED METHODS OF ASSEMBLY/DISASSEMBLY

[75] Inventors: Howard Tran, Santa Clara; Roland Jeffrey Wyatt, San Jose; Gilbert Lima, Fremont, all of Calif.

[73] Assignee: General Electric Company, Milwaukee, Wis.

[21] Appl. No.: 09/205,822

[22] Filed: Dec. 4, 1998

[51] Int. Cl.⁷ ...................................................... A61B 8/14
[52] U.S. Cl. ............................................................ 600/459
[58] Field of Search ................................... 600/446, 459; 73/633, 644, 621–626; 257/712; 361/704

[56] References Cited

U.S. PATENT DOCUMENTS

| | | | |
|---|---|---|---|
| 4,149,419 | 4/1979 | Connell, Jr. et al. | 73/621 |
| 5,213,103 | 5/1993 | Martin et al. | 600/443 |
| 5,560,362 | 10/1996 | Silwa, Jr. et al. | 600/439 |
| 5,721,463 | 2/1998 | Snyder | 310/334 |
| 5,779,639 | 7/1998 | Yeung | 600/446 |
| 5,961,465 | 10/1999 | Kelly, Jr. et al. | 600/459 |

*Primary Examiner*—Marvin M. Lateef
*Assistant Examiner*—Ali M. Imam
*Attorney, Agent, or Firm*—Dennis M. Flaherty; Christian G. Cabou; Phyllis Y. Price

[57] ABSTRACT

A repairable compact ultrasound probe which is easy to assemble and disassemble, and which has cable load transfer and heat dissipation capabilities. The transducer assembly of the probe has a heat-conductive backing board which is fastened to a yoke incorporated in the cable assembly. The cable assembly further has a strain relief element which is secured in a separate operation following attachment of the yoke to the backing board. When the strain relief element is secured, the probe handle is compressed between the strain relief and a headshell of the transducer assembly, thereby forming a housing. To disassemble the probe, the strain relief is turned counterclockwise with respect to the transducer, thereby releasing the handle and allowing access to the probe interior.

17 Claims, 2 Drawing Sheets

ULTRASOUND PROBE AND RELATED METHODS OF ASSEMBLY/DISASSEMBLY

FIELD OF THE INVENTION

This invention generally relates to probes used in ultrasonic imaging of the human anatomy. In particular, the invention relates to methods and techniques for manufacturing an ultrasound probe.

BACKGROUND OF THE INVENTION

A conventional ultrasonic probe comprises a transducer pallet (hereinafter "transducer") which must be supported within the probe housing. A conventional transducer comprises a linear array of narrow transducer elements, each made of piezoelectric material. Typically, each transducer element has metallic coatings on opposing front and back faces to serve as ground and signal electrodes respectively. The signal electrodes are typically connected to respective electrical conductors formed on a flexible printed circuit board.

When a voltage waveform is developed across an electrode during transducer operation, the piezo-electric material vibrates at a frequency corresponding to that of the applied voltage, thereby emitting an ultrasonic wave into the media to which the piezoelectric element is coupled. Conversely, when an ultrasonic wave impinges on an element, the piezoelectric material produces a corresponding voltage across its terminals and the associated electrical load component of the electrical source.

The transducer also comprises a mass of suitable acoustical damping material having high acoustic losses positioned at the back surface of the element array. The backing layer is acoustically coupled to the rear surface of the transducer elements, via the acoustically transparent PCB, to absorb ultrasonic waves that emerge from the back side of each element so that those waves will not be partially reflected and interfere with the ultrasonic waves propagating in the forward direction.

Typically, the front surface of each transducer element of array is covered with at least one acoustic impedance matching layer. The impedance matching layer transforms the high acoustic impedance of the transducer elements to the low acoustic impedance of the human body and water, thereby improving the coupling with the medium in which the emitted ultrasonic waves will propagate.

The transducer element array, backing layer and acoustic impedance matching layer are all bonded together in a stack-up arrangement. A lens material is then cast around the transducer stack-up. During assembly of the ultrasonic probe, the transducer stack-up with lens cast thereon is secured in the probe housing using adhesive.

In conventional applications, each transducer element produces a burst of ultrasonic energy when energized by a pulsed waveform received from a transmitter in the associated imaging system via a coaxial wires connected to the flexible PCB. This ultrasonic energy is transmitted by the probe into the tissue of the object under study. The ultrasonic energy reflected back to transducer element array from the object under study is converted to an electrical signal by each receiving transducer element and sent separately to a system receiver, again via the coaxial wires and the PCB. The release of acoustic energy during transmission creates a thermal buildup in the probe due to acoustic losses being converted into heat. The amount of heat that can be allowed to build up on the exterior of an ultrasound probe must be within prescribed limits. Typically the limit is that the temperature on the patient contact surface of the probe cannot exceed 16° C. above ambient temperature or 41° C., whichever is smaller. Most of the heat tends to build up immediately around the transducer elements, which are necessarily situated in the probe very close to the body of the patient being examined.

Conventional thermal management in ultrasound probes is accomplished with relatively simple devices such as heat pipes, which are buried in the transducer structure so that they transfer heat from the source into the body of the probe structure as quickly as possible. In this way heat is piped from the critical front surface of the probe into the handle where the increased mass helps dissipate the heat evenly.

For example, U.S. Pat. No. 5,545,942 discloses the employment of foil heat conductors made of heat conductive, electrically nonconductive material. The foil heat conductors are placed around the periphery of the transducer (but within the probe housing) so that heat can be drawn away from the transducer face and toward the rear/interior of the probe. These heat conductors act as conduits for draining heat from the thermal potting material which fills the spaces inside the probe housing. Thus, the heat conductors are effectively thermally coupled to the transducer element array. This arrangement increases the ability to dissipate heat away from the transducer and thus away from the patient being examined. U.S. patent application Ser. No. 08/343,063 also discloses that the internal heat pipes can be thermally coupled to the shielding braid of the cable. Because the shielding braid is made of tin/copper, connecting the heat pipes to the shielding braid facilitates the wicking away of even more heat from the transducer element array. By soldering the overall shield into a metal foil structure which is in contact with the internal heat pipes, heat generated by the transducer can be piped into the cable and dissipated throughout the 2-m length of the cable. Internal potting with thermally conductive epoxy also helps provide additional contact to the shield and the individual shields of the individual signal coaxial wires inside the cable.

U.S. Pat. No. 5,721,463 discloses a device for improving thermal transfer inside an ultrasound probe and reducing heat buildup near the transducer face. The cable components are used as heat pipes which conduct heat out of the probe handle. The cable assembly in an ultrasonic probe is composed of multiple coaxial wires bundled together and covered with an overall braided shield. The shield is in turn encased by a cable jacket made of polymeric material. Each individual coaxial wire comprises a plurality of individual conductors surrounded by a twisted shield. These heat conductive structures serve as thermal transfer devices when thermally coupled to an internal heat pipe, made of a sheet or plate of heat conductive material, which is embedded in the backing layer material of the transducer. Thus, heat generated by the transducer array can be transferred, via the internal heat pipe and the cable heat pipes, away from the probe surface which contacts the patient. The coaxial cable also has a bundle of strands or fibers made of a high-tensile-strength polymeric material (e.g., nylon) arranged in the center of the cable (e.g., surrounded by a circular array of signal coaxial wire bundles) and running the length of the cable. This central bundle of nylon strands reinforces the cable to withstand tensile loads thereon.

Many conventional probes are also difficult to assemble and bulky, making them expensive to manufacture and uncomfortable to the patient and user during scanning. Previous probes used permanent adhesive that required special fixture and time for proper curing, and was messy to work with. Moreover, although probes which are not bulky have been made for specific applications, these probes are not repairable because of the permanent adhesive. Thus there is a need for a repairable compact ultrasound probe which is easy to assemble and disassemble. In addition, such a probe should have cable load transfer and heat dissipation capabilities.

SUMMARY OF THE INVENTION

The present invention is a repairable compact ultrasound probe which is easy to assemble and disassemble, and which has cable load transfer and heat dissipation capabilities. The probe comprises a handle and two major assemblies: a cable assembly and a transducer assembly. The transducer assembly has a heat-conductive backing board which is fastened to a yoke incorporated in the cable assembly. The cable assembly further comprises a strain relief element which is secured in a separate operation following attachment of the yoke to the backing board. When the strain relief element is secured, the probe handle is compressed between the strain relief and a headshell of the transducer assembly, thereby forming a housing.

The probe in accordance with the preferred embodiment of the invention uses fewer parts than comparable conventional probes. Using the strain relief system design, the probe can be assembled without using any permanent adhesive. Existing probe designs do not allow access to the probe's interior for repair due to the use of permanent adhesive during assembly. As a result, most defective probes are disposed of, which is wasteful. In contrast, the probe in accordance with the preferred embodiment, in addition to being easy to assemble, is repairable. To allow access to the probe interior, it is only necessary to turn the strain relief counterclockwise with respect to the handle and then slide the strain relief and the handle up the cable to expose the yoke/backing board connection. Then the backing board can be disconnected from the yoke, thereby disconnecting the cable and transducer assemblies from each other. As a result of these simple steps, a repair person can gain access to the probe interior and perform the required repair. This design of the strain relief system allows one to easily access the probe interior without damaging either the housing or the circuitry.

The preferred embodiment of the probe also incorporates a cable load transfer capability. Typically when one pulls on the cable, the tensile force transfers directly to the probe and to the signal coaxial wires. Without any distribution of this force, the coaxial wires could ultimately break away from the probe from continuous use. The design of the yoke includes a feature to transfer the load on the cable from the outer coaxial shield to the yoke, and ultimately to the handle and the headshell. In particular, the outer coaxial shield and the jacket of the cable are fastened to the yoke with a metal band. As a result of this feature, the tensile load on the cable is sustained by the yoke, instead of the signal coaxial wires. Through the arrangement of the yoke and the transducer assembly, the tensile force is further distributed to the handle and the headshell. This is preferred because the signal coaxial wires are not subjected to the strain from the pull on the cable.

The preferred embodiment of the probe further incorporates a heat dissipation capability. The transducer generates heat during scanning, which could make the patient uncomfortable. By choosing a material having a high coefficient of thermal conductivity, heat dissipation away from the patient can be maximized. Accordingly, the backing board, the yoke and the insert are all made of an aluminum alloy. The backing board, yoke, metal band and outer coaxial shield, connected in series to the transducer, form a heat sink which directs thermal energy away from the transducer and distributes it to the whole length of the cable. Since heat is removed from the transducer, which contacts the patient, patient comfort is improved.

The method for assembling an ultrasound probe in accordance with the preferred embodiment comprises the following steps: 1) threading an end of an electrical cable through a strain relief system; 2) sliding the strain relief system up the electrical cable; 3) threading the end of the electrical cable through a handle; 4) connecting the end of the electrical cable to a coupling element; 5) connecting a transducer assembly to the coupling element; 6) moving the handle relative to the cable until the handle abuts the transducer assembly; 7) sliding the strain relief system down the electrical cable until the strain relief system engages the coupling element; and 8) threadably coupling the strain relief system to the coupling element until the handle is securely pressed between the strain relief system and the transducer assembly.

The method for disassembling an ultrasound probe in accordance with the preferred embodiment comprises the following steps:

DETAILED DESCRIPTION OF THE PREFERRED EMBODIMENTS

Figure 2:
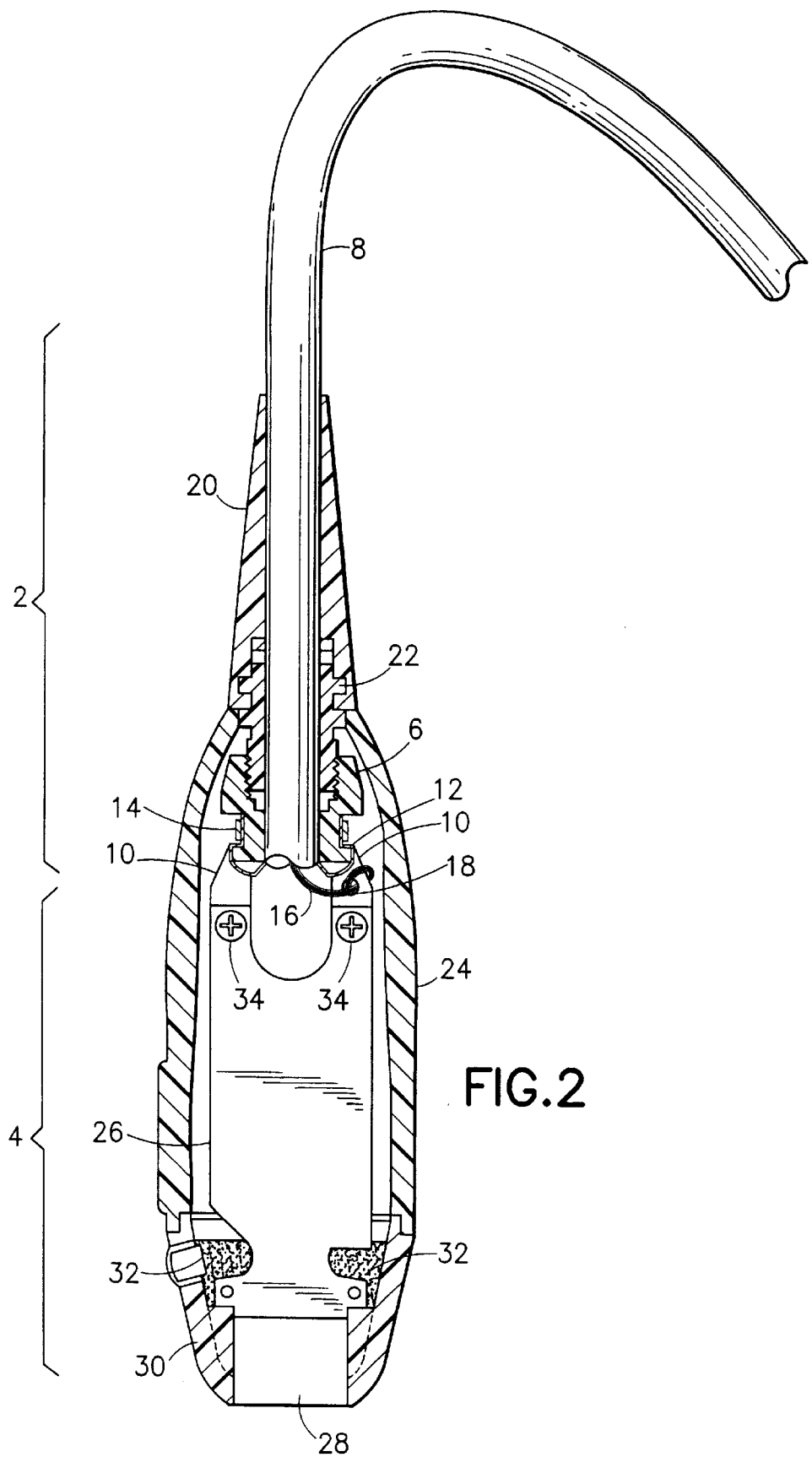
FIG. 2 is a schematic showing a cross-sectional view of the ultrasound probe of FIG. 1 in a fully assembled state.

Referring to FIG. 2, the ultrasound probe in accordance with the preferred embodiment of the invention comprises two major assemblies: a cable assembly 2 and a transducer assembly 4. The cable assembly 2 comprises a yoke 6 made of an aluminum alloy and a cable 8 having a portion which passes through an unthreaded portion of a central bore in the yoke 6. The yoke has two arms 10. The central bore of yoke 6 also has a threaded portion for threadably coupling with an insert, as described below. Along the portion of the cable 8 which extends beyond the yoke and connects to the flexible printed circuit boards (not shown), an outer coaxial shield 12 is peeled back and wrapped around one end of the yoke 6 in a manner such that the shield and yoke are in heat conductive relationship. The wrap-around portion of shield 12 is attached to the yoke 6 by means of a circular metal band 14, which crimps the shield inside an external annular groove formed in yoke 6. Preferably, the groove has a width greater than the width of the metal band to allow the band to seat inside the groove. In addition, the distal end of the central bundle of nylon strands 16 is threaded through a hole 18 in one of the yoke arms 10 and then tied to the yoke.

The cable assembly further comprises a strain relief element 20 made of elastic polymeric material, which is molded to an insert 22 made of aluminum alloy. The insert 22 has a generally circular cylindrical structure with a pair of annular projections extending radially outward; an unthreaded central bore through which the cable passes; and a threaded outer circumferential surface on one end thereof. The first annular projection interlocks with the strain relief molded therearound. The second annular projection provides a seat for one end of the handle 24.

Again referring to FIG. 2, the transducer assembly comprises an aluminum alloy backing board 26 having one end embedded in an acoustic damping material (not shown) at the back of a transducer 28, making them a rigid subassembly. For the sake of clarity, the transducer circuitry is not shown. The transducer form fits into an opening in a headshell 30. Epoxy adhesive 32 is used to secure the transducer/backing board subassembly to the headshell 30 to form a rigid transducer assembly 4.

In accordance with the preferred embodiment, the yoke 6 has a pair of arms 10, each arm having a threaded hole. Similarly, the backing board 26 has a pair of arms, each arm having an unthreaded hole. The arms of the yoke are fastened to the respective arms of the backing board by means of a pair of screws 34, thereby attaching the cable assembly 2 to the transducer assembly 4. In addition, the threaded end of insert 22, with strain relief element 20 molded thereto, is screwed into the threaded end of yoke 6. In this final assembly, the handle 24 is compressed between the strain relief element 20 and the headshell 30 of the transducer assembly. The headshell 30 and handle 24 form a housing which surrounds backing board 26, yoke 6, insert 22, and the connections of the ends of the signal coaxial wires with the terminals of the flexible PCBs (not shown in the drawings).

Figure 1:
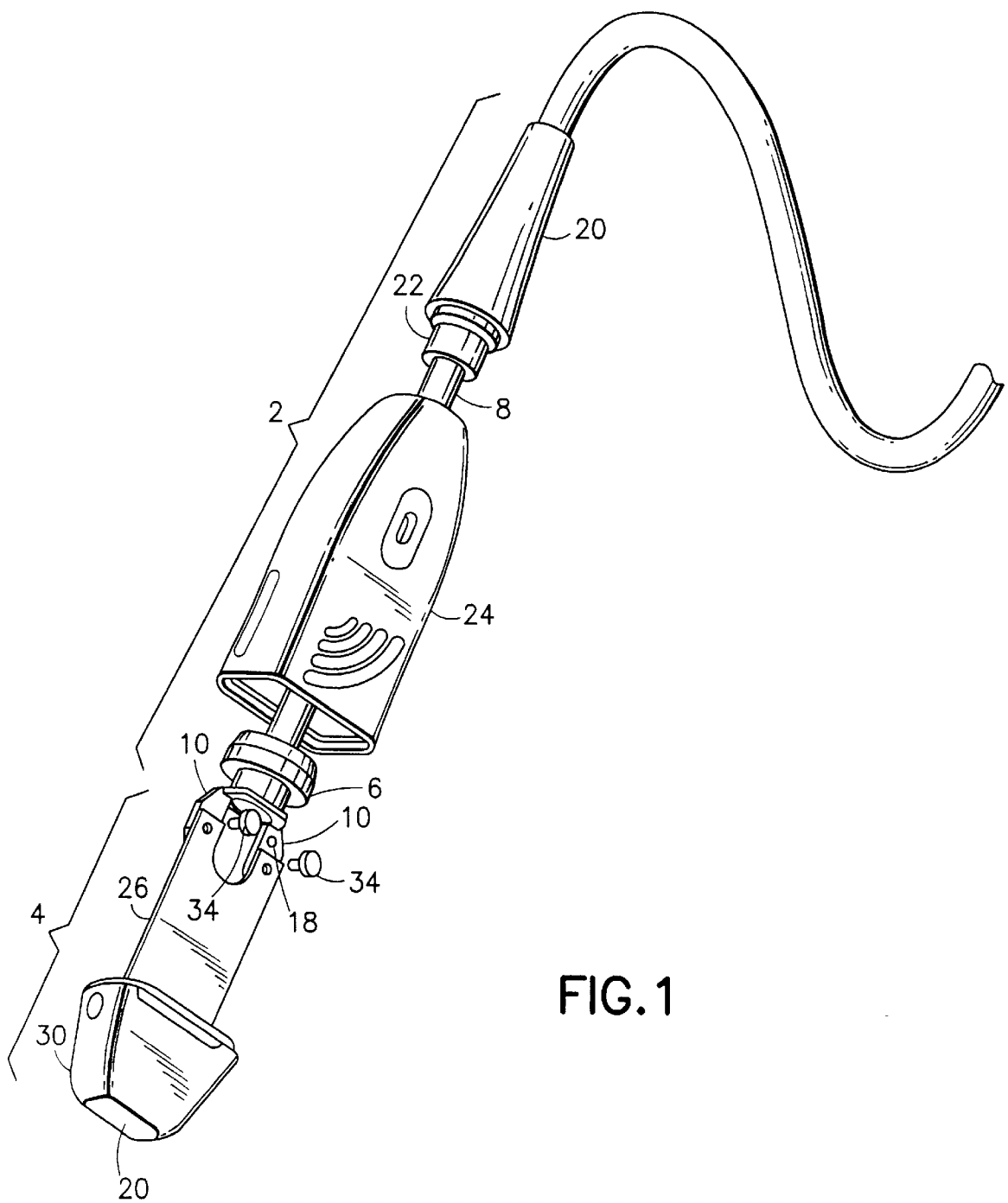
FIG. 1 is a schematic showing an isometric view of a partially assembled ultrasound probe in accordance with the preferred embodiment of the invention, with signal coaxial wires and printed circuit boards not shown for the sake of clarity.

The probe in accordance with the preferred embodiment is designed to facilitate easy assembly and disassembly. one stage in the assembly/disassembly operation is depicted in FIG. 1.

To assemble the probe, the strain relief 20 is molded onto the insert 22 to form a strain relief/insert subassembly, and the acoustic backing layer is molded onto the back of the transducer 28 and the end of the backing board 26 to form a transducer/backing board subassembly. The distal end of the cable 8 is threaded through a circular cylindrical hole in the strain relief and a circular cylindrical bore in the insert. Then the cable end is passed through the handle 24. The relative positions of the strain relief/insert subassembly and the handle at this stage are depicted in FIG. 1. Lastly, the end of the cable is passed through the central bore of the yoke 6 and the outer coaxial shield and cable jacket are peeled back and wrapped around the unthreaded end of the yoke 6, which has an annular groove on its outer circumferential surface. A metal band 14 is then installed to crimp the wrap-around portion of the outer coaxial shield 12 inside the annular groove in the yoke, thereby attaching the yoke to the cable.

Probe assembly is completed by fastening the transducer assembly 4 to the cable assembly 2 (with strain relief system retracted) by screwing the backing board 26 to the yoke 6 with the handle 24 loosely surrounding the cable 8 (this stage in the assembly process is shown in FIG. 1); moving the handle 24 into its final position snug against the headshell 30; sliding the strain relief system 20/22 along the cable 8 until the insert 22 engages the yoke 6; and then screwing the insert 22 into the yoke 6. This last step causes the handle 24 to be compressed between the headshell 30 and the strain relief 20, making one complete rigid assembly.

As discussed above, the strain relief element 20 is secured in place by an operation independent of the fastening of the cable and transducer assemblies, namely, by rotating the strain relief system (20/22) in a clockwise direction to screw the insert 22 into the yoke 6. Consequently, to disassemble the probe it is necessary to rotate the strain relief system in the counterclockwise direction to unscrew the insert 22 from the yoke 6 and then slide the strain relief system up the cable 8 to free the handle 24. Then the handle is slid up the cable to provide access to the yoke/backing board connection. The transducer assembly can be uncoupled from the cable assembly by simply unfastening the screws 26 which connect the yoke 6 to the backing board 26. The uncoupled transducer assembly is then accessible for repair.

The above-described structure provides both cable load transfer and heat dissipation capabilities. As a result of the attachment of the outer coaxial shield and the central bundle of nylon strands to the yoke, the tensile load on the cable is sustained by the yoke, instead of the signal coaxial wires. Through the connection of the yoke to the transducer assembly, the tensile force is further distributed to the handle and the headshell. In addition, the aluminum alloy backing board, the aluminum alloy yoke, the metal band and the outer coaxial shield, connected in series to the transducer, form a heat sink which directs thermal energy away from the transducer and distributes it to the whole length of the cable.

As used in the claims, the term "ultrasound transducer" refers to a structure comprising an array of transducer elements and optionally one or more layers of other materials having other functions, such as acoustic matching, acoustic damping and so forth.

The foregoing preferred embodiments have been disclosed for the purpose of illustration. Variations and modifications of the concept of the invention will be readily apparent to persons skilled in the art. All such variations and modifications are intended to be encompassed by the claims set forth hereinafter.

What is claimed is:

1. An ultrasound probe comprising:

at probe housing having an end;

an ultrasound transducer seated in said probe housing;

a transducer support structure having first and second portions, said first portion being mechanically coupled to said transducer;

a strain relief subsystem penetrating said end of said probe housing and having a passage;

an electrical cable passing through said passage in said strain relief subsystem; and a first mechanical coupling element mechanically coupled to said strain relief subsystem and to said second portion of said transducer support structure, and having a passage penetrated by said electrical cable.

2. The probe as recited in claim 1, wherein said strain relief system comprises a second mechanical coupling element and an elastic strain relief molded to said second mechanical coupling element, said first and second mechanical coupling elements being threadably coupled to each other, and said second mechanical coupling element having a bore penetrated by said electrical cable.

3. The probe as recited in claim 1, wherein said probe housing comprises a headshell and a handle, said transducer being seated in said headshell, and said handle being compressed between said strain relief system and said headshell, and said strain relief system being rotatable relative to said headshell.

4. The probe as recited in claim 1, wherein said transducer support structure and said first mechanical coupling element are made of a heat-conductive material.

5. The probe as recited in claim 1, wherein said heat-conductive material is an aluminum alloy.

6. The probe as recited in claim 1, wherein said electrical cable comprises a bundle of strands which run along a length of said electrical cable, said bundle of strands being attached to said first mechanical coupling element.

7. The probe as recited in claim 1, wherein said electrical cable comprises a heat-conductive structure extending along a length of said electrical cable, further comprising a heat sink assembly arranged inside said probe housing, said heat sink assembly having one end connected to said transducer and another end connected to said heat-conductive structure of said electrical cable, wherein said heat sink assembly comprises said first mechanical coupling element made of heat-conductive material, an end of said heat-conductive structure of said electrical cable being attached to said first mechanical coupling element.

8. The probe as recited in claim 7, wherein said heat-conductive structure of said electrical cable comprises an outer shield having an end folded back and wrapped around an end of said first mechanical coupling element.

9. The probe as recited in claim 8, wherein said heat sink assembly further comprises a metal band arranged on the exterior of said end of said first mechanical coupling element to hold said end of said outer shield in place.

10. The probe as recited in claim 7, wherein said heat sink assembly further comprises a backing plate made of heat-conductive material, and having one end connected to said first mechanical coupling element and another end connected to said transducer.

11. The probe as recited in claim 10, wherein said first mechanical coupling element comprises first and second arms, and said one end of said backing plate comprises first and second arms, further comprising first and second removable fasteners for respectively fastening said first and second arms of said first mechanical coupling element to said first and second arms of said backing plate.

12. The probe as recited in claim 10, wherein said first mechanical coupling element and said backing plate are made of aluminum alloy.

13. An ultrasound probe comprising:

a probe housing;

an ultrasound transducer seated in said probe housing;

a transducer support structure having first and second portions, said first portion being mechanically coupled to said transducer;

a strain relief subsystem in contact with said probe housing;

an electrical cable penetrating said strain relief system and said probe housing; and a first mechanical coupling element mechanically coupled to an end of said electrical cable, to said strain relief subsystem and to said second portion of said transducer support structure, wherein said electrical cable comprises an outer shield having an end folded back and wrapped around a portion of said first mechanical coupling element, further comprising a metal band for holding said end of said outer shield of said electrical cable against said portion of said first mechanical coupling element.

14. An ultrasound probe comprising:

a probe housing;

an ultrasound transducer seated in said probe housing;

a transducer support structure having first and second portions, said first portion being mechanically coupled to said transducer;

a strain relief subsystem in contact with said probe housing;

an electrical cable penetrating said strain relief system and said probe housing; and a first mechanical coupling element mechanically coupled to an end of said electrical cable, to said strain relief subsystem and to said second portion of said transducer support structure, wherein said first mechanical coupling element comprises first and second arms, and said second portion of said transducer support structure comprises first and second arms, further comprising first and second removable fasteners for respectively fastening said first and second arms of said first mechanical coupling element to said first and second arms of said transducer support structure.

15. An ultrasound probe comprising:

a handle having first and second ends;

an electrical cable penetrating said first end of said handle;

an assembly penetrating said second end of said handle, and comprising an ultrasound transducer and a first threaded coupling element penetrated by said cable; and a device penetrating said first end of said handle, and comprising a second threaded coupling element penetrated by said cable and adapted for coupling with said first threaded coupling element, wherein said handle is pressed securely between said assembly and said device when said first and second threaded coupling elements are threadably coupled, and said second threaded coupling element is slidable along said cable.

16. The probe as recited in claim 15, wherein said device further comprises strain relief molded to said second coupling element, and said assembly further comprises a headshell in which said ultrasound transducer is seated, wherein said handle is pressed securely between said strain relief and said headshell when said first and second coupling elements are coupled.

17. The probe as recited in claim 15, wherein said assembly further comprises a backing plate connected to said first coupling element and to said ultrasound transducer, wherein said backing plate is connected to said first coupling element by removable fasteners.

* * * * *